United States Patent [19]

Kimura et al.

[11] 4,453,125

[45] Jun. 5, 1984

[54] MICROWAVE ALCOHOL FUEL SENSOR

[75] Inventors: Katsuhiro Kimura, Tokyo; Akira Endo, Mito; Takanori Shibata, Hitachi; Hiroshi Morozumi, Tokyo, all of Japan

[73] Assignee: Hitachi, Ltd., Tokyo, Japan

[21] Appl. No.: 397,899

[22] Filed: Jul. 13, 1982

[30] Foreign Application Priority Data

Jul. 15, 1981 [JP] Japan ................................. 56-109369

[51] Int. Cl.³ ...................... G01R 27/04; G01R 27/26
[52] U.S. Cl. ............................. 324/58.5 A; 324/61 R
[58] Field of Search ........... 324/61 R, 58.5 R, 58.5 A, 324/58.5 B, 58.5 C, 316, 300; 73/61.1 R

[56] References Cited

U.S. PATENT DOCUMENTS

| | | | |
|---|---|---|---|
| 2,703,079 | 3/1953 | Argento | 324/58.5 A X |
| 3,508,145 | 4/1970 | Reed | 324/58.5 A |
| 3,691,454 | 9/1972 | Hrubesh | 324/58.5 C X |

*Primary Examiner*—Stanley T. Krawczewicz
*Assistant Examiner*—Jose M. Solis
*Attorney, Agent, or Firm*—Antonelli, Terry & Wands

[57] ABSTRACT

A microwave alcohol fuel sensor comprises a microwave oscillator, a microwave receiver, and a microwave transmission circuit connected to the oscillator and the receiver. The microwave transmission circuit comprises a dielectric substrate and, a strip line mounted on the substrate so that microwaves leak from the substrate to an alcohol gasoline fuel, and the microwaves attenuate by alcohol dielectric loss, whereby output voltage from the receiver corresponds to alcohol content rate. The dielectric substrate is formed tubular so that a constant amount of the fuel is fed the sensor.

16 Claims, 13 Drawing Figures

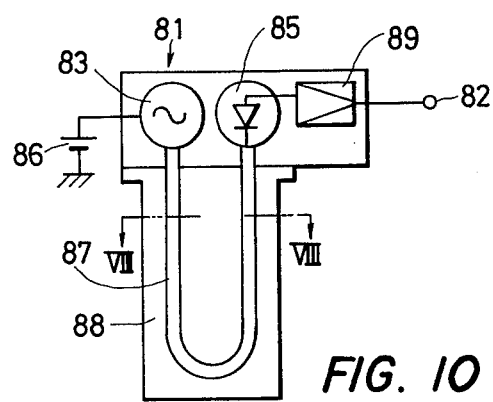
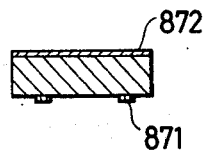
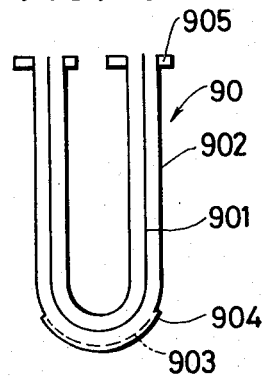
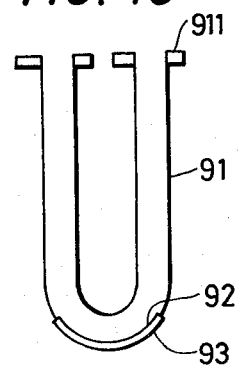
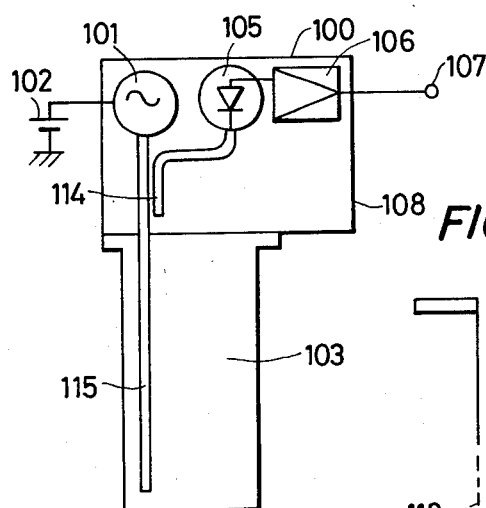
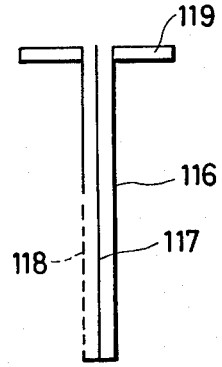
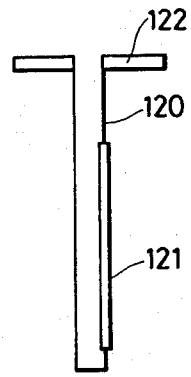

MICROWAVE ALCOHOL FUEL SENSOR

BACKGROUND OF THE INVENTION

This invention relates to a microwave alcohol fuel sensor, and more particularly to a microwave alcohol fuel sensor for automobile internal combustion engines.

Recently, alcohol fuel has come into notice as fuel for automobile internal combustion engines in place of gasoline fuel. The alcohol fuel is advantageous in that the fuel can be used for present automobiles without changing greatly the constructions and that an amount of atmosphere pollution substances into which the fuel is converted by the combustion of the fuel are less than the gasoline fuel.

One of the alcohol fuels is a mixture of alcohol and gasoline. When such a mixture is used, it is important to detect precisely the mixing ratio and to run the engine under the most appropriate condition. In order to satisfy the above, it is necessary to develop a practical method of simply and precisely measuring the mixing ratio or the alcohol content.

Various methods of measuring the mixing ratio are proposed. When the methods are really used in automobiles, however, they should meet various requirements of the automobiles. At present, therefore, an electrostatic capacity method of the various methods is most likely to put into practice. According to the electrostatic capacity method, the mixing ratio is measured by detecting output voltage established between a pair of parallel electrodes disposed in the fuel. However, the change in the output voltage level according to alcohol content rate is very small, for example 1.7 volt at the maximum. Further, the output voltage changes much greater at relatively small alcohol content rate than at large content rate. Therefore, it seems that improvements should be put into this method to effect a precise measurement.

SUMMARY OF THE INVENTION

An object of the invention is to provide a microwave alcohol fuel sensor which is simple in construction and which can measure precisely the alcohol content rate in an alcohol-containing fuel such as an alcohol-gasoline mixture fuel.

Briefly stated, a microwave alcohol fuel sensor according to the invention is characterized in that a microwave transmission circuit for transmitting microwaves from a microwave oscillator to a microwave receiver has a microwave leakage portion contacting an alcohol-containing fuel such as an alcohol-gasoline mixture so that microwaves or electromagnetic field leaks from the microwave leakage portion into the fuel and alcohol dielectric loss takes place whereby voltage corresponding to the alcohol content rate is detected by the microwave receiver.

BRIEF DESCRIPTION OF THE DRAWINGS

FIG. 7 is a front view of another embodiment of a microwave alcohol fuel sensor according to the invention;

FIG. 8 is a sectional view taken along a line VIII—VIII of FIG. 7;

FIGS. 9 and 10 are modifications of a microwave transmission circuit of FIG. 7, respectively;

FIG. 11 in a front view of another embodiment of a microwave alcohol fuel sensor according to the invention; and FIGS. 12 and 13 are modifications of a resonator of FIG. 11, respectively.

DESCRIPTION OF THE PREFERRED EMBODIMENTS

Figure 1:
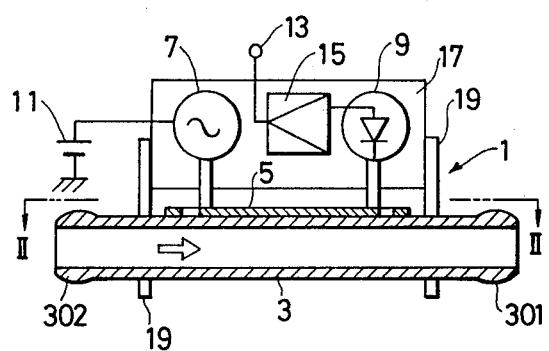
FIG. 1 is a sectional view of an embodiment of a microwave alcohol fuel sensor according to the invention.

Referring to the drawings an embodiment of a microwave alcohol fuel sensor 1 according to the invention will be described in detail hereinafter.

Figure 2:
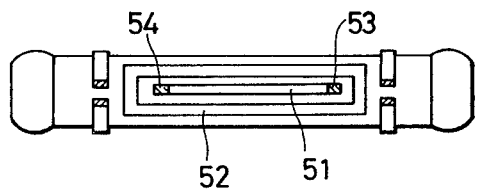
FIG. 2 is a sectional view taken along a line II—II of FIG. 1.

In FIG. 1, a tubular member 3, which serves as a part of a fuel pipe, is made of a dielectric and has connecting ends 301, 302. On the surface of the tubular member 3, a coplanar type strip line 5 is provided. The strip line 5, as shown in FIG. 2, axially extends and consists of a central conductor 51 and an earth conductor 52 surrounding the central conductor 52 with a distance spaced from each other. The strip line 5 is connected to a microwave oscillator 7 and a microwave receiver 9 at the ends 53, 54 of the central conductor 51. The oscillator 7 which comprises a Gunn diode, an IMPATT diode, or a high-frequency transistor is connected to an electric source 11 and the receiver 9 is connected to a terminal 13 through an amplifier 15. The oscillator 7, the receiver 9, and the amplifier 15 are all mounted on a substrate 17 which is secured to a pair of fixing members 19 fixed to the tubular member 3.

The dielectric, forming the tubular member 3 which is $1 \sim 2$ mm thick, is a solid substance having dielectric constant of about $2 \sim 15$ and dilectric loss angle of about $10^{-3} \sim 10^{-5}$, such as plastic or ceramic. Particularly, the ceramic tube is preferable for a precise measurement because of very little deformation due to temperature and pressure changes. The strip line 5 is formed on the tubular member 3 by thick-film printing, conductive thin-film adhesion, or the like.

Figure 5:
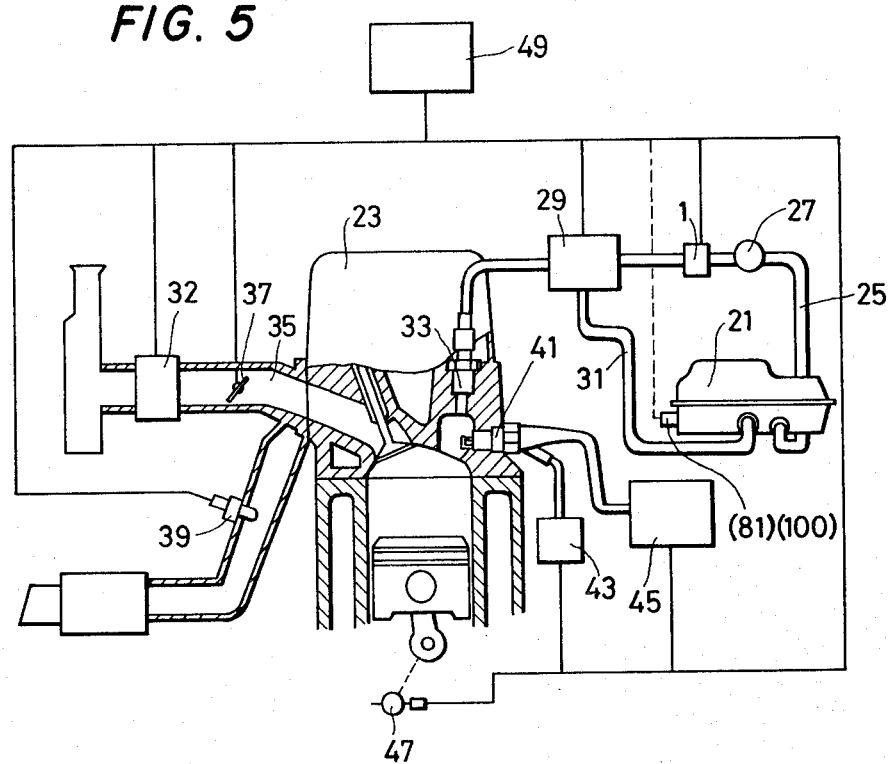
FIG. 5 is a schematic diagram of an automobile internal engine control system.

The microwave alcohol fuel sensor, is incorporated into, for example, a fuel supply line of an automobile internal engine control system as shown in FIG. 5.

In FIG. 5, fuel of an alcohol-gasoline mixture is conveyed from a fuel tank 21 to an automobile internal combustion engine 23 through the fuel supply line 25. The line 25 is provided with a pump 27, a fuel injection controller 29, a fuel return line 31 and a fuel injector 33. The sensor 1 is mounted on the line 25 between the pump 27 and the fuel injection controller 29 by fitting the ends 301 and 302 of the tubular member 3 of the sensor 1 to the line 25, so that the interior of the tubular member 3 is filled fully with the fuel.

On the other hand, air is introduced into the engine 23 through an air flow meter 32 provided in an air induction passage 35 and a throttle sensor 37, and an exhaust gas is exhausted out of the engine 23 through a $O_2$ sensor 39. An ignition plug 41 which is mounted on the engine 23 is provided with an ignitor 45 and a pressure sensor 43. The ignitor 45, the pressure sensor 43, the microwave alcohol fuel sensor 1, the fuel injection controller 29, the air flow meter 32, the throttle sensor 37, the O₂ sensor 39 and a crank angle detecting sensor 47 are connected electrically to a computer 49 so that an amount of fuel to be injected into the engine 23, ignition timing, etc. are controlled according to output from the computer which generates the output, based on signals from the abovementioned sensors and the meter.

The microwave alcohol fuel sensor 1 mounted on the fuel supply line 25, as abovementioned, is in contact with the fuel to be detected for alcohol content. Under this condition, electric waves are generated by the microwave oscillator 7. The waves propagate on the strip line 5 and reach the microwave receiver 9. An electromagnetic field, which takes place when the microwaves propagate, leaks into the fuel through the dielectric tubular member 3. The leaked microwave is absorbed or attenuated by alcohol dielectric loss in the fuel so that the level of the microwaves which reach the microwave receiver 9 changes according to the content rate of the alcohol. The output of the microwave receiver 9 is amplified by the amplifier 15 and is transmitted to the terminal 13.

In this embodiment, the tubular member 3 is always filled with fuel to be detected so that dielectric loss does not change according to an amount of fuel, but changes mainly according to the alcohol content rate. The strip line 5 extends axially, therefore an amount of attenuation of microwaves can be chosen freely so that precise sensor can be achieved.

Figure 6:
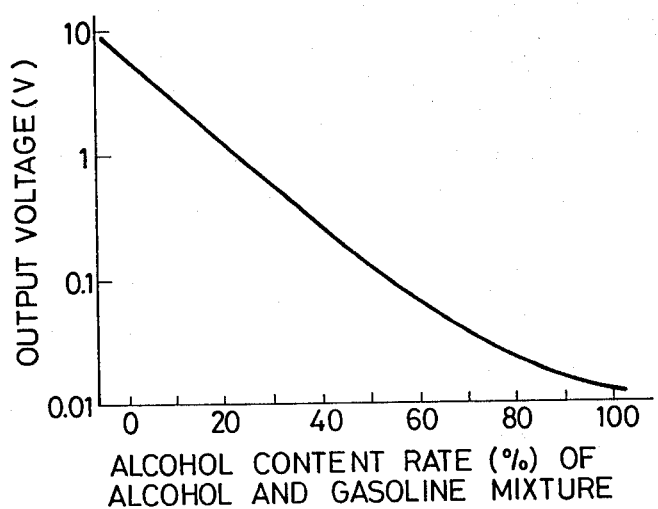
FIG. 6 is a graph showing a relation between an output voltage of a microwave receiver and the alcohol content rate of an alcohol-gasoline mixture fuel.

Referring to FIG. 6, there is shown a graph of a relation between output voltage of the microwave receiver 9 and alcohol content rate of an alcohol-containing fuel mixture.

From the graph, it is noted that change of output voltage runs into about four figures between 100% gasoline and 100% alcohol, and is approximately linear therebetween.

Another embodiment of the invention will be described in FIGS. 3 and 4.

Figure 3:
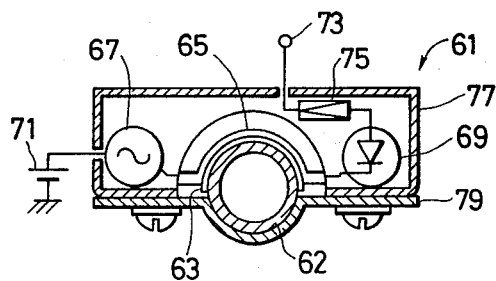
FIG. 3 is a sectional view of another embodiment of a microwave alcohol fuel sensor according to the invention.
Figure 4:
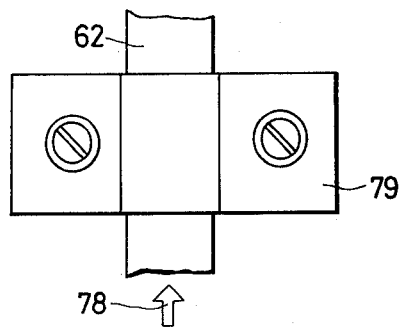
FIG. 4 is a under view of FIG. 3.

In FIG. 3, a microwave alcohol sensor 61 has a construction such that the sensor 61 can be mounted on a fuel pipe 62 from the outside of the pipe 62. The fuel pipe 62 is made of dielectric at least a part thereof. A dielectric substrate 63 extends arcuately along a part of the periphery of the pipe 62 and it is fixed to contact tightly with the pipe 62. On the arcuate substrate 63 a coplanar type strip line 65 which is the same as in FIG. 1, except that the strip line is arcuate is mounted, one end of the strip line 65 is connected to a microwave oscillator 67 of the same kind as abovementioned which is connected to an electric source 71. The other end of the strip line 65 is connected to a microwave receiver 69 which is connected to a terminal 73 through an amplifier 75. The oscillator 67, the substrate 63, the receiver 69 and the amplifier 75 are all contained in and fixed to a casing 77. The casing 77 is fixed to the pipe 62 by means of a retaining plate 79 and screws so that the arcuate substrate 63 tightly contacts the surface of the pipe 62.

Microwaves generated by the oscillator 67 propagate to the receiver 69 along the strip line 65. During the propagation, an electromagnetic field leaks into the fuel being conveyed in pipe 62 through the dielectric portion of the fuel pipe 62 and is attenuated through alcohol dielectric loss so that the output level of the receiver 69 decreases mainly according to the alcohol content rate of the fuel, as shown in FIG. 6.

This embodiment of the microwave alcohol fuel sensor 61 according to the invention is easily mounted by replacing a part of a conventional iron fuel pipe with a fuel supply system for the dielectric substance such as ceramic, plastic, or the like, and by means of the screws and the retaining plate. This sensor 61 also shows the same characteristics of output voltage of the receiver 69 to the alcohol content rate of an alcohol-containing fuel mixture as in FIG. 6, and is incorporated into the fuel supply line at the same position as the above sensor shown in FIG. 5.

Further another embodiment of a microwave alcohol fuel sensor according to the invention will be described in detail hereinafter.

Referring to FIG. 7, a microwave alcohol fuel sensor 81 is provided with a microwave oscillator 83, such as that used in the embodiment of FIG. 1. The oscillator 83 is connected to an electric source 86 to be operated thereby. Oscillating frequency in a microwave region of about 1~30 G Hz is used in which the circuit is easily handled in view of the relation of oscillation elements and resonance circuit. Electric waves of the oscillator 83 propagate in a strip line 87 provided on a dielectric substrate 88 and reach a microwave receiver 85. The strip line 87 is a circuit comprising a central conductor 871 and an earth conductor 872 which are thin films formed on the front and back faces of the dielectric substrate, and being constructed so that the electromagnetic field of the microwaves leak from the dielectric substrate 88. The dielectric substrate 88 is secured to a plate mounting thereon the oscillator 83, the receiver 85, and an amplifier 89 connected to a terminal 82.

This sensor 81 is dipped into a fuel of alcohol-fuel mixture to the extent that at most the entire fuel contacts the strip line 87. Microwaves leaked are absorbed through alcohol dielectric loss, and the level of microwaves which reach the microwave receiver 85 changes according to the concentration of alcohol in the fuel. Output of the receiver 85 is amplified by the amplifier 89 and put out to the terminal 82.

This strip line 87 can be replaced for other circuit without changing the characteristic.

In FIG. 9, a coaxial circuit 90 is shown which comprises a coaxial central line 901 and a coaxial outer conductive member 902. The outer conductive member 902 which is cylindrical is provided with a window 903 for leaking electric waves and a dielectric member 904 is used for sealing the window. The waves leak into fuel surrounding the coaxial circuit 90 through the window 903 and is subject to microwave attenuation by the fuel. Flanges 905 at the ends are used for connecting the circuit 90 to a microwave oscillator and a microwave receiver.

In FIG. 10, another example of a transmission circuit is shown, wherein the circuit comprises a waveguide 91 which is rectangular or circular in shape. The waveguide 92 also has an electric wave leakage window 91 which is sealed by a dielectric member 93. Ends 911 are connected to the microwave oscillator and the microwave receiver, respectively, as abovementioned.

Further another embodiment of a microwave alcohol fuel sensor according to the invention is described hereinafter referring to FIG. 11.

In FIG. 11, a junction circuit 114 is connected to a microwave oscillator 101, which is electrically connected to an electric source 102. One side of the junction circuit 114 is connected to a strip line 115 which has a terminal end shorted at an integral multiple of half the microwave length, and another is connected to a microwave receiver 105.

Electric waves from the microwave oscillator 101 propagate to the terminal end shorted strip line 115. In this case, the strip line 115 operates as a resonator of ½ wavelength, and electromagnetic field leaked therefrom also is more than the other strip line. Therefore, attenuation characteristic increases when the strip line 115 is dipped into an alcohol-gasoline mixture, and the level change of microwaves reflected from the strip line 115 is larger. The reflected microwaves are introduced into the microwave receiver 105 by the junction circuit 114, and the voltage corresponding to a mixing ratio of the fuel is obtained.

In this construction, the strip line 115 is provided on a dielectric substrate 103 which is connected to a plate 108 mounting thereon the microwave oscillator 101, the microwave receiver 105, and an amplifier 106 connected to the receiver 105 for amplifying voltage signals and putting out them to a terminal 107.

When a terminal end shorted coaxial circuit which comprises an outer line 116 with an electric wave leakage slit 118 sealed by dielectric material, a central line 117, and connecting portion 119, as shown in FIG. 12, or a terminal end shorted waveguide 120 with a microwave leakage slit 121 sealed by a dielectric member is used instead of the strip line 115, the same characteristic can be obtained as if the strip line 115 was used.

The microwave alcohol fuel sensors shown in FIGS. 7 and 11 can also be incorporated in the fuel tank 21 as shown in FIG. 5, whereby the sensors are always in contact with the fuel in the tank 21.

As abovementioned, the microwave alcohol fuel sensor according to the invention is simple in construction, and provides a large output voltage level, whereby a high precise measurement can be effected.

What is claimed is:

1. A microwave alcohol fuel sensor for measuring the alcohol content of an alcohol-gasoline fuel mixture, which comprises:
    a microwave oscillator which generates microwaves and is connected to an electric power source;
    a microwave receiver; and
    a microwave transmission means for transmitting microwaves from said microwave oscillator to said microwave receiver, said microwave transmission means including a dielectric portion contacting the alcohol-gasoline fuel mixture, whereby microwaves are leaked into the alcohol-gasoline fuel mixture and the microwaves which reach said microwave receiver vary according to the content of alcohol in said alcohol-gasoline fuel mixture.

2. A microwave alcohol sensor for measuring alcohol content of an alcohol-gasoline fuel, which comprises:
    a tubular member for conveying the alcohol-gasoline fuel, said tubular member having at least a portion made of dielectric material through which microwaves can propagate from the outside into the alcohol-gasoline fuel;
    a microwave oscillator disposed outside said tubular member and connected to an electric power source;
    a microwave receiver disposed outside said tubular member;
    a strip line that is electrically connected to said microwave oscillator and said microwave receiver so as to form a microwave transmission means, and that is positioned on the outside of said tubular member so that microwaves leaked from said microwave transmission means propagate into the fuel through said portion of said tubular member, said strip line comprising two conductors spaced laterally from each other.

3. The sensor as set forth in claim 2, wherein said strip line extends along the axis of said tubular member.

4. The sensor as set forth in claim 2, wherein said strip line extends along the periphery of said tubular member.

5. The sensor as set forth in claim 2, wherein said tubular member comprises dielectric pipe which is a part of fuel supply line of an internal engine, further including an arcuate dielectric member mounted on said tubular member, and said type strip line being mounted on said arcuate dielectric member.

6. The sensor as set forth in claim 1, wherein said microwave transmission means comprises a dielectric substrate, an earth conductor provided on a front side of said dielectric substrate and a central conductor provided on the other side opposite to the front side, said means including a projecting portion that is dipped into an alcohol-gasoline fuel mixture.

7. The sensor as set forth in claim 1 wherein said microwave transmission means comprises a junction circuit, and a terminal end shorted strip line connected to one end of the junction circuit opposite to the shorted terminal end.

8. The sensor as set forth in claim 2, wherein said tubular member is joined to a fuel supply line of an internal combustion engine whereby said tubular member is always filled with fuel.

9. The sensor as set forth in claim 2, wherein said tubular member is made of ceramic.

10. The sensor as set forth in claim 2, wherein said strip line comprises a central conductor surrounded by an earth conductor so that the two conductors are spaced laterally from each other.

11. The sensor as set forth in claim 10, wherein said microwave oscillator and said microwave receiver are connected to opposite ends of said strip line.

12. The sensor as set forth in claim 2, wherein said strip line is of a coplanar type and is provided on the outer surface of said tubular member so that said microwaves which are leaked from said microwave transmission means propagate into said alcohol-gasoline fuel mixture through said dielectric portion of said tubular member.

13. The sensor as set forth in claim 2, wherein the thickness of said tubular member is 1–2 mm.

14. The sensor as set forth in claim 2, wherein said dielectric which forms said tubular member is a solid substance having a dielectric constant of about 2–15 and a dielectric loss angle of about $10^{-3}$ to $10^{-5}$.

15. The sensor as set forth in claim 2, wherein said tubular member is joined to a fuel supply line of an internal combustion engine under pressure, wherein the interior of said tubular member is filled with a stream of the fuel.

16. The sensor as set forth in claim 6, wherein an oscillating frequency is used which is in a microwave region of about 1–30 GHz.

* * * * *